United States Patent [19]

Ringlien

[11] Patent Number: 4,610,542
[45] Date of Patent: Sep. 9, 1986

[54] SYSTEM FOR DETECTING SELECTIVE REFRACTIVE DEFECTS IN TRANSPARENT ARTICLES

[75] Inventor: James A. Ringlien, Maumee, Ohio
[73] Assignee: Owens-Illinois, Inc., Toledo, Ohio
[21] Appl. No.: 672,036
[22] Filed: Nov. 16, 1984
[51] Int. Cl.[4] ............................................. G01N 21/90
[52] U.S. Cl. .................... 356/240; 209/526; 250/223 B
[58] Field of Search ............................. 356/239, 240; 250/223 B; 209/524, 526

[56] References Cited

U.S. PATENT DOCUMENTS

| | | | |
|---|---|---|---|
| 3,199,401 | 8/1965 | Sleighter et al. | 250/572 X |
| 3,245,533 | 4/1966 | Rottmann | 250/223 B |
| 3,302,787 | 2/1967 | Rottmann | 250/232 B |
| 3,932,042 | 1/1976 | Faani et al. | 356/240 |
| 4,175,236 | 11/1979 | Juvinall | 250/223 B X |
| 4,378,493 | 3/1983 | Dorf et al. | 250/223 B |
| 4,487,322 | 12/1984 | Juvinall | 356/240 X |

Primary Examiner—Davis L. Willis
Assistant Examiner—Matthew W. Koren
Attorney, Agent, or Firm—John R. Nelson

[57] ABSTRACT

A system of back illuminating a glass container with generally horizontal collimated light having a vertical gradient of brightness produced by placing a showcase light behind the upper area of a diffuser plate.

The light passing through the bottle is imaged by a lens into the region of the entrance aperture of a camera having a vertical array of pixels. The lens in the camera is focused on the side of the bottle. The output of the camera will be of a general level equal to the level of illumination of the middle of the diffuser. When a refractive defect in the bottle deflects light from the brightest area of the diffuser into the aperture of the camera, the signal output will rise, and if light from the darkest area of the diffuser is deflected by the defect into the aperture of the camera, the output signal will be substantially less. Thus, the output signal provides a way to discriminate between two types of refractive defects, and by filtering the output signal, the background noise can be eliminated, leaving only the characteristic more abrupt signal produced by a defect.

6 Claims, 11 Drawing Figures

BOTTLE WALL

SYSTEM FOR DETECTING SELECTIVE REFRACTIVE DEFECTS IN TRANSPARENT ARTICLES

BACKGROUND OF THE INVENTION

In the detection of optical defects in glass articles, such as bottles or jars, it has been the practice to illuminate the jars, usually with a diffuse backlight, and view the container either optically or with a light sensitive pickup.

One such disclosure is U.S. Pat. No. 4,378,493 dated Mar. 29, 1983, where a system for illuminating the full height of a container placed in an inspection position is shown and described. The source disclosed consists of a plurality of incandescent bulbs behind a frosted glass plate, thus producing generally a relatively large diffuse source for backlighting the container in the inspection position. With this diffuse backlighting arrangement, the side of the container adjacent the light, which may have refractive defects in it, will not enter into or affect the light emanating from the forward or opposite wall of the container to any appreciable extent. A vertical, linear array camera, focused on the front wall of the container, will provide an image of the wall onto the vertical array of pixels in the camera. The pixels then are serially interrogated and adjacent pixels are compared with respect to their output, which is a function of the light received thereon, and in this manner, light which is reflected or sufficiently refracted by defects in the container wall in view of the camera, will be made apparent by the output of the linear array. Of course, this particular arrangement requires rotation of the container about its vertical axis in order to provide a circumferential scan of the entire container side wall and viewing area, which may also include the neck and shoulder area of the container. In this system, when a reflective defect, such as a check or an absorptive defect, such as a stone, appears in the wall of a container, as that portion of the wall is moved through the viewing area of the camera, the pixels upon which the wall is being focused will see areas of darkness caused by the reflection or absorption of the illuminated light out of the line of sight of the pickup. In this way, as previously stated, by comparing the output of adjacent pixels one can determine where the defect lies in a vertical plane and also to a great extent can determine the size of the defect as well. The pixels are scanned at a sufficient rate so that essentially every area of the bottle is viewed and most defects actually will span more than a single scan and will appear in several successive scans.

It should be remembered, however, that the light which reaches the forward wall of the container has come from a diffuse source of finite extent and therefore the intensity of the defect region is not materially affected by most light refracting effects in the object. This is particularly apparent when one considers that most optical inspection systems which are looking for dirt in the bottom of the container use a differ source positioned below the upright container so that lettering, such as factory and mold numbers, will not be visible from above the container where the optical transmission analyzer is located.

It has also been the practice to optically detect defects, such as checks, in various portions of glass articles by focusing a beam of light onto an area of the article at a particular angle and then positioning a pickup, such as a photocell, at approximately a 90° angle with respect to the direction of the focused light. In this arrangement, such as is shown in U.S. Pat. No. 3,245,533, the light will be reflected from the defect onto the photocell, thus indicating the presence of a reflective defect. This has been the typical system for examining the finish and heel portions of glass containers in the past and the focused light will be reflected by a check into the photocell as the container is rotated about its vertical axis, in station, where the inspection setup is provided. It should be understood that the defects which are being detected are those typically termed checks caused usually by thermal shocks during the formation of the container generally by the touching of the hot glass after forming by a cold piece of handling equipment. Generally speaking, checks are reflective if their opposed surface separation is at least a half wave length of light. If the separation is less than a half wave length, the light would pass through and the defect would not reflect light and therefore not be detectable. Another defect which is picked up by the use of specular, focused light are those surface defects produced in glass containers which will cause the focused light to be refracted out of the direction in which it is being transmitted to the container and the placing of the pickups at positions such that refraction, for example, from a "line-over-finish" defect, such as illustrated in U.S. Pat. No. 3,302,787, will be detected.

In the inspection of flat glass articles such as television faceplates or architectural glass, it has been customary to illuminate the article with a beam of focused light and then sweep the focused light across the width of the article while moving the article at right angles to the scanning beam. In this way, nearly all of the glass surfaces will be covered. The light passing through the article is picked up by a complementary scanning photocell. Such a system is shown in U.S. Pat. No. 3,199,401 to Pittsburgh Plate Glass Co. It should be noted that the system requires that an angular illumination be used to avoid reflections that might give erroneous readings. The movement of slightly wavy appearing surfaces into the view of the light and pickup will cause refraction of the focused light and result in the pickup being without illumination during these periods. Whether these are commercially unacceptable becomes a matter of concern, and it would be advantageous to have an inspection system where the defects that are of the type which make the product unsatisfactory for its intended purpose, are enhanced and discriminated from those refractive effects that are not severe.

In order to provide special illumination techniques, one may employ a space invariant system as disclosed and claimed in copending application Ser. No. 634,930, filed July 24, 1984, the disclosure of which is incorporated herein by reference thereto.

In the above cited application, a diffuse source of uniform illumination intensity is provided with a hard edge mask over the source which limits the distribution of ray directions or angular spectrum of the plurality of collimated beams produced.

OBJECTS AND SUMMARY OF THE INVENTION

In view of the foregoing, it is an object of the present invention to provide method and apparatus for inspecting and sorting transparent articles, such as glass containers, which are economical to implement due to the special illumination technique used, capable of discrimination and which are effective for sorting acceptable commercial ware from defective unacceptable ware.

In accordance with the present invention, a system is provided for optically illuminating transparent glass objects for the purpose of detecting optical defects in the objects. The disclosed system of illumination provides for a space-invariant illumination of the objects that are moved through the field of view of the optical pickup.

Therefore, it is an object of the present invention to inspect objects for refractive defects by using a diffuse source placed at the focal plane of a lens to produce a plurality of "collimated beams" traveling in a continuum of different directions with the result of illuminating the object to be inspected with a tailorable distribution of ray directions, or angular spectrum.

It is a further object of the present invention to back illuminate the object with a gradient light intensity, then view the object with a linear array camera and analyze the signals received by the camera so as to detect those defects which are refractive in nature and of a certain slope and providing grey scale detection to discriminate between certain defects by the signals from the camera.

It is a still further object of the present invention to provide a system of detecting optical defects, such as stones and buried blisters in glass objects, by back illuminating the object with a space invariant system having a gradient intensity while moving the object relative to the source and observing variations in transmitted light intensity passing out of the object by a line-scan camera.

DETAILED DESCRIPTION OF THE DRAWINGS

Figure 1:
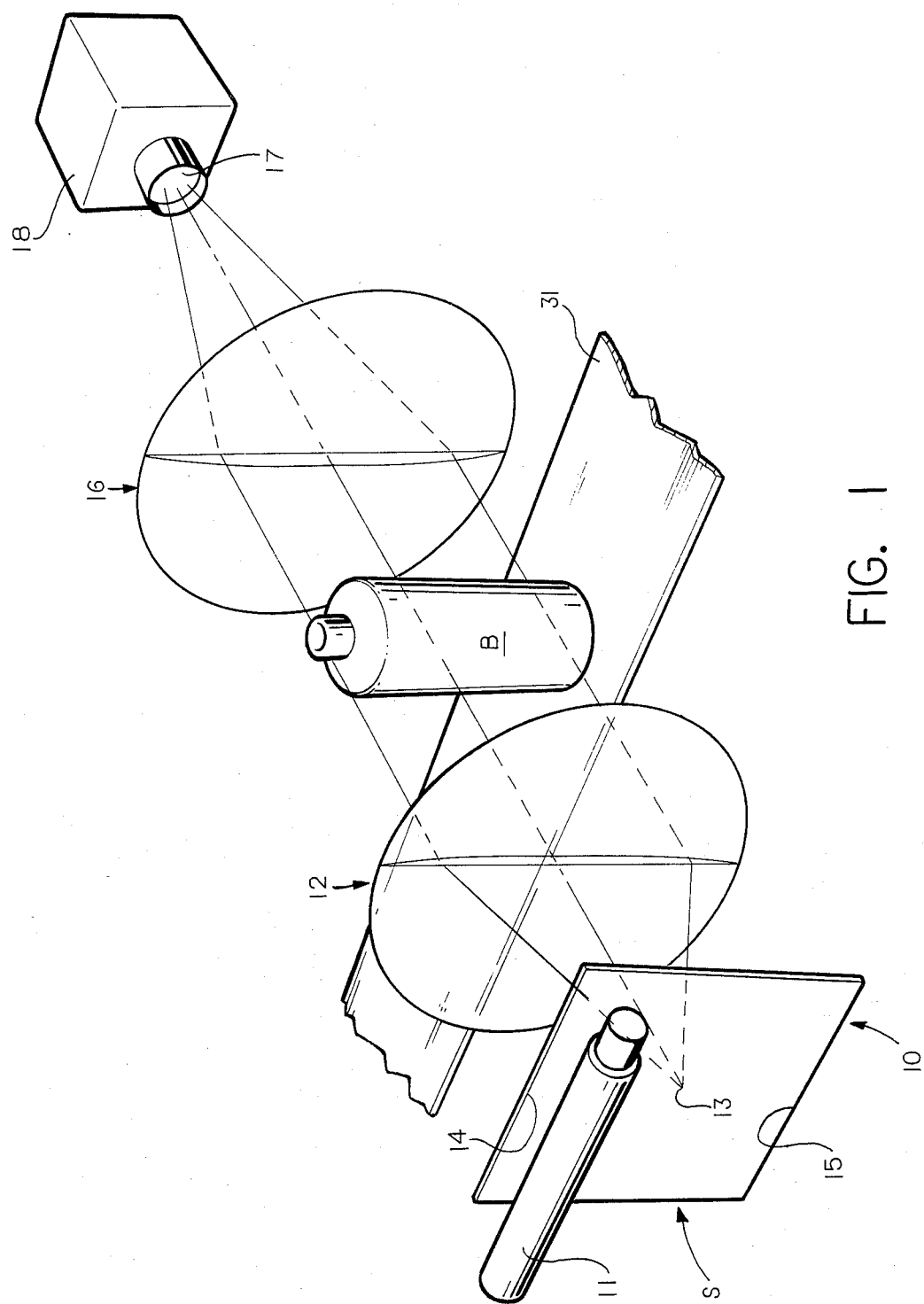
FIG. 1 is a schematic, perspective view of one embodiment of the apparatus of the invention.

In the forming of transparent ware on typical glass forming machines, a number of optical defects which do not totally absorb light may appear in the ware. Those defects may be the type which will refract or reflect a beam of light out of a particular direction. The refractive defects may be caused by a bulge or bump in the surface of the container or bottle. Also, a blister or void within the wall of the bottle will refract light out of a normal path and "seeds", which are small blisters, will refract a light beam. "Settle wave" is another light refractive surface condition that may occur in a bottle sidewall resulting in a horizontal thickened area about the circumference of a bottle made by the blow and blow process. The "settle wave" is positioned about the bottle in the lower half of the sidewall and is caused by the chill produced in the parison by the settle blow against the baffle resulting in an annular area in the parison that is more viscous and thus does not expand as evenly as the rest of the parison when it is blown into the form of the finished container.

"Checks" or "cracks" are examples of light reflective defects that may be produced in bottles during manufacture. These are usually the result of a thermal stress induced in the blown container due to the touching of the hot glass with handling equipment. "Checks" produce mirror-like areas in the glass and are usually detected by their reflectance of a directed beam of specular light.

The detection of refractive defects in objects of simple geometry, such as a flat plate glass, would seem to be relatively straightforward. By back illuminating such a plate with a focused light beam and then imaging, in transmitted light, the plate with an optical system of limited acceptance angle, regions of the plate which refract light out of the beam entering the optical system will appear dark. The sensitivity to defects, of such a system, will depend upon the acceptance angle of the imaging optics and on the angularity of the illumination. However, the detection of refractive defects in objects of more complex shapes, such as glass containers, presents a problem of another magnitude. Containers will refract light from a specular beam due simply to their basic geometric shape, not necessarily due to any specific defect. In addition, the inner surface of a glass container is free-formed and therefore this inner surface is subject to considerable surface shape variations in perfectly acceptable commercial ware. The appearance of these surface shape variations will generally obviate techniques such as the one described above for the flat plate.

In order to provide an illumination which would be optically detectable, it would appear that a more angularly rich source, such as a diffuse source, would be necessary. As indicated previously, it is known that in detecting defects which absorb light, unwanted effects due to refraction can, to a large extent, be averaged out by using isotropic back illumination and imaging the object in transmission. If one is to inspect, for example, the approximately cylindrical side wall of a transparent container where a source is on the opposite side, the illumination of the container will have to be viewed after it has passed through two walls of the container. However, when using a generally diffuse source, the appearance of the container wall closest to the viewing system will not appreciably differ from that which would result with the far wall not being present. Thus, for the sake of clarity, one can mentally eliminate the far wall and in essence consider an inspection concept with reference to a system in which essentially only one wall is being viewed. Most machine made glass containers have what is termed a "settle wave" which appears generally below the median height of the container and yet above the heel area. This "settle wave" is produced when the glass is blown from the parison shape into final bottle shape and is due to a condition where the glass in one annular area of the parison adjacent the baffle is normally colder and thus does not expand as evenly as other areas of the parison. This produces, in the side wall of the container, a somewhat thicker annular area in the glass. The "settle wave" generally is an appearance problem and, if it is not severe, it normally does not affect the commercial utility of the container. The "settle wave" can be termed a gradual, refractive, optical disturbance in the side wall of the container.

As schematically shown in FIG. 5 of U.S. application Ser. No. 634,930 cited above, which is a representation, in two dimensions, of the transmission of light through a section of a glass article as viewed by a camera 10 having an acceptance angle gamma and imaging the vicinity of point C of the article. If the inner surface of the article is planar, that is, as shown by the dashed line 12, the light appearing to come from point C originates at the source area A. If, however, the inner surface is non-planar, as illustrated by the solid line 14, the viewing axis is, in effect, refracted by an angle $\theta$ and light appearing to come from point C actually originates at the source area A'. If the source 16 has uniform brightness and is isotropic, the apparent brightness of point C will be essentially unaffected, in the absence of absorption, by the depicted refraction. On the other hand, this refraction could be detected by masking area A', for example at the right of line 18, thus making this area nonemitting, in which case the image of point C would appear dark against a bright field. Refractive defects are then detected by means of decreases in the apparent transmission of points such as C, as if they were absorptive defects.

The use of masks, however, has limited applicability in defect detection because the use of masks is not space invariant. The appearance of a given defect will depend upon the relative positions of point C and the edge 18 of the mask, thus making the appearance of the defect depend upon its transverse location in the field and upon the longitudinal distance of the object from the mask. Thus, even a moderate refractive error in one portion of the field can produce a reduction in transmission equal to that obtained for a larger refractive error in another portion of the field. Thus, the system is space variant. These limitations can be circumvented, however, by insuring that the apparent transmission of the point C is dependent only upon the angle $\theta$ through which the viewing axis is refracted. As suggested by the foregoing, back illuminating the object with a source of uniform brightness over its surface and finite extent, the light transmission intensity will be independent of the location of the point A' on the source and, thus, the relative positions of point C and A', yielding the desired space invariance.

Using a newly devised technique, a vertical intensity distribution may be produced at the diffused source which is converted to an angular distribution at the sample side of a lens, the task of selectively rendering invisible the gradual surface variations can be performed optically. Since these variations generally refract the viewing axis through small angles, they are unobservable if the source intensity distribution or angular spectrum is uniform in these small angles.

Figure 2:
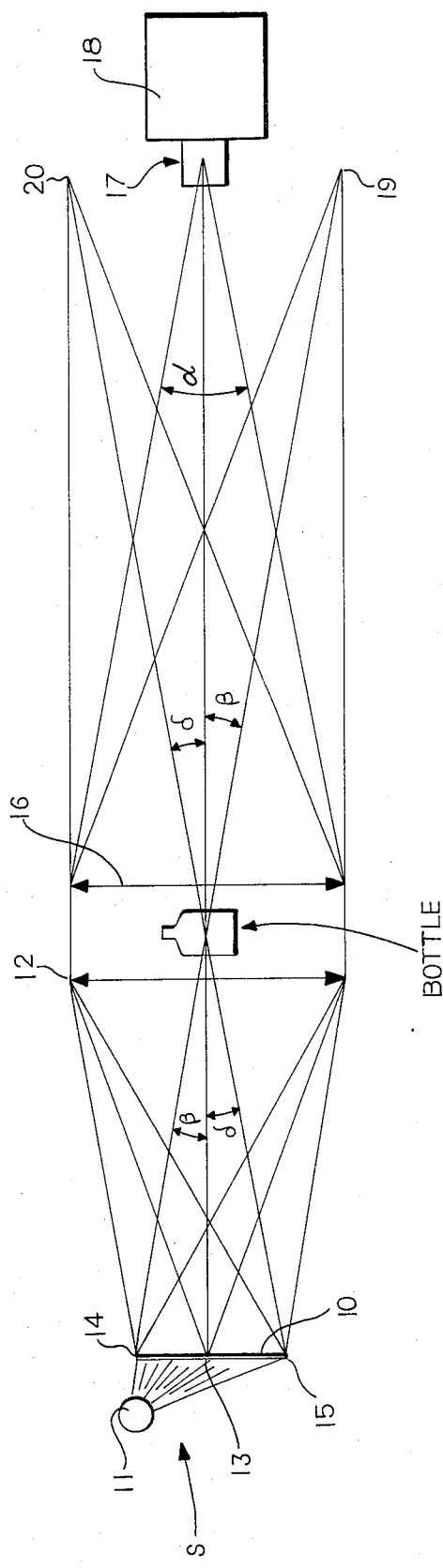
FIG. 2 is a schematic, side elevational view of the apparatus of FIG. 1.

With particular reference to FIGS. 1 and 2, there is schematically shown the optical implementation of a tailorable source having the desired angular spectrum. A diffuse source generally designated S in the form of a frosted plate 10 positioned in front of an elongated filament lamp 11 is placed at the focal point of a lens 12. The gradient light source is used to produce a signal that is proportional to the slope of refractive variations in a bottle wall. Since the gradient is in the vertical direction because of the position of the lamp 11 being adjacent the top of the diffuser 10, an upper area 14 on the diffuser will be the brightest area while a lower area 15 will be the darkest. A middle area 13 will have an average brightness and falls along the optical axis of the lens 12. Each unobstructed point such as 13, 14 and 15 on the source S then results, in a plane in frort of the lens 12, in a collimated beam which extends parallel .to a line through the point and the center of the lens. Since the source is isotropic and of non-uniform brightness, each beam will contain a different flux density. The angular spectrum of illumination in front of the lens will be limited to angles equal to or less than $\beta+\delta$.

A second lens 16 is placed several inches from lens 12 to receive the collimated light from lens 12 and bring it into focus near a lens 17 of a linear array camera 18. A bottle B to be inspected is moved between the lenses 12 and 16. The lens 17 of the camera 18 is focused on the bottle wall nearest to it. Light from any point on the diffuser 10 is collimated by the lens 12 and brought to a focus near the camera lens 17 by the second lens 16. For example, the points 14 and 15 on the diffuser are imaged at points 19 and 20, respectively, near the camera lens.

As illustrated in FIG. 2, the point 13 on the diffuser 10 where the optic axis of the system intersects the diffuser will be imaged into the entrance pupil of the lens 17 by lens 16. The field of view $\alpha$ of the camera is such that it will see uniform brightness because of the characteristic of the midpoint 13 of the diffuser. Light from the darkest area 15 and brightest area 14 will be imaged as 20 and 19, respectively, near the camera lens. These rays, however, will miss the aperture of the camera lens 17. Thus, the linear array, which is vertical in the camera 18, will have a uniform voltage output signal indicating a uniform brightness.

As can be seen, the gradient of light on the diffuser 10, in combination with the lens 12, produces an angle-to-intensity relationship in the region between the lenses 12 and 16 where the bottle is shown, wherein the angle-to-intensity relationship of this illumination is such that the intensity varies smoothly from a maximum at angle $\beta$ to a minimum at angle $\delta$. One example of the system to illuminate the diffuser is shown in FIGS. 1 and 2 in the form of the elongated, linear showcase lamp, with points or areas 13 and 15 being successively farther from the lamp.

Other systems could be used, such as a gradient filter placed at the back of the diffuser with a full array of lamps covering the area of the filter. The gradient in the filter may duplicate the effect of the showcase lamp 11 shown in FIGS. 1 and 2. Other and more complex systems could be used as well to give the uniform gradient of illumination on the diffuser.

Figure 3A:
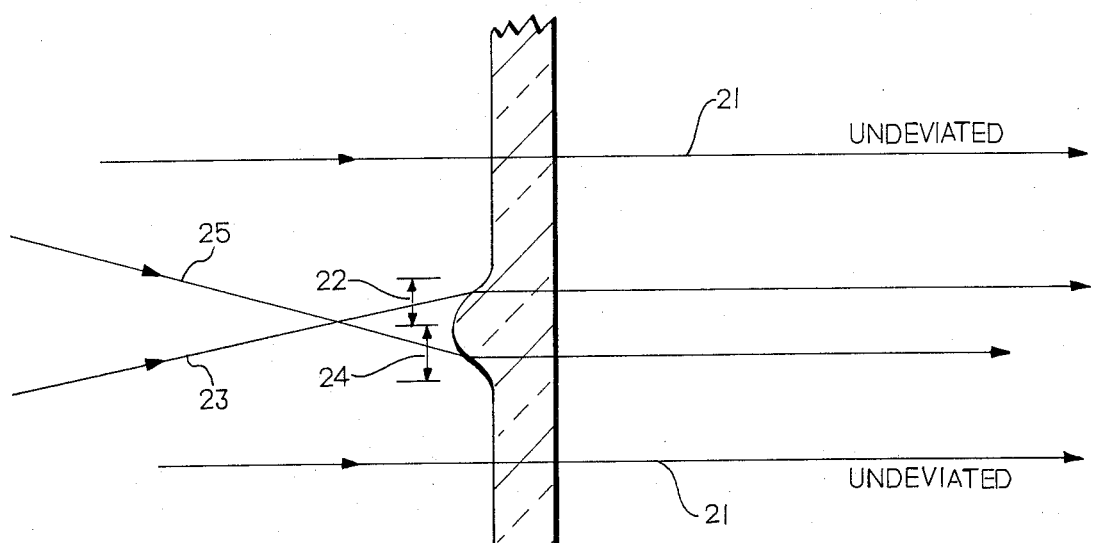
FIG. 3(a) is a partial cross-sectional view on an enlarged scale of bottle side wall illustrating light ray deflection.
Figure 3B:
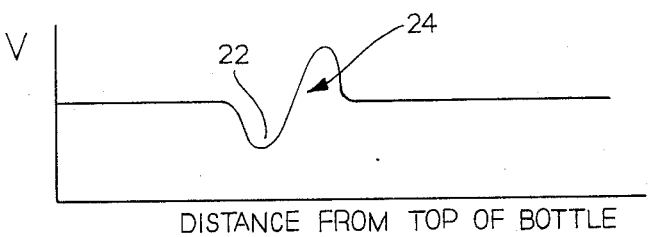
FIG. 3(b) is a graphic illustration of the transmissivity readings obtained from FIG. 3(a) viewing.

Turning now to FIGS. 3(a) and 3(b), one may consider what happens when a bottle with a defect moves into the region between the lenses 12 and 16. The illustrated defect is in the form of a protruding lump. The majority of the wall is sufficiently uniform configuration to pass the collimated light relatively undeviated (see arrows 21 FIG. 3(a)) and will look uniformly grey to the linear array camera which scans down. The region designated 22 on the lump acts like a wedge and will deflect light (arrow 23) from the darkest area of the diffuser 10 into the camera so that the camera will see less light in this region and the signal will be lower for this region. Similarly, the region designated 24 will deflect light (arrow 25) from the brightest part of the diffuser 10 into the camera and the signal output will go up.

FIG. 3(b) is an illustration of the signal output for a down scan by the camera. The regions 22 and 24 correspond to the areas of the bottle so designated in FIG. 3(a). The steeper the slope of the defect, the greater the contrast in the output of the camera will appear relative to the background level.

Figure 4A:
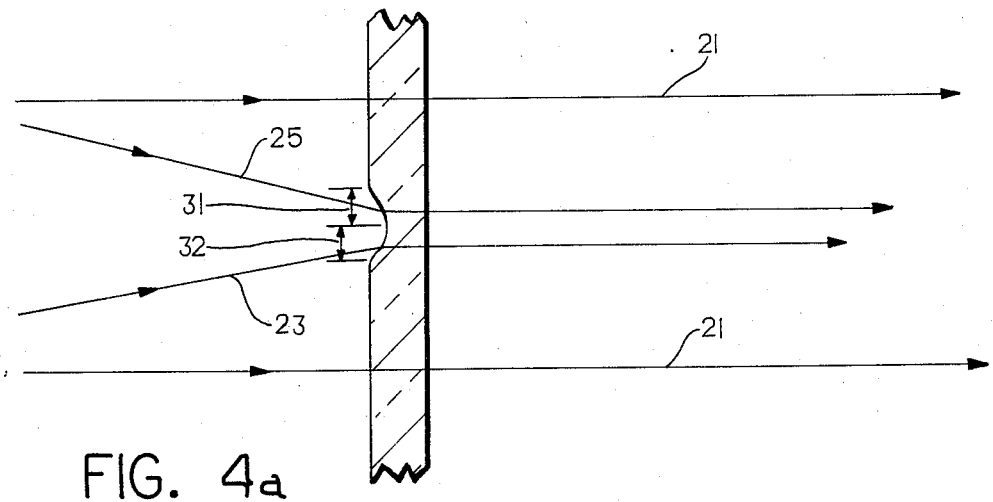
FIG. 4(a) is a partial cross-sectional view, on an enlarged scale, of a bottle side wall illustrating light ray deflection.
Figure 4B:
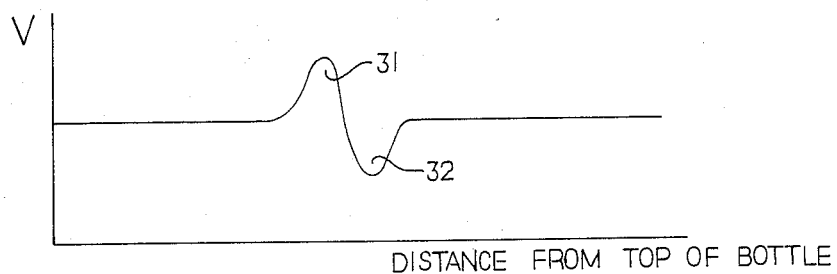
FIG. 4(b) is a graphic illustration of the optical transmissivity readings obtained from the viewing of FIG. 4(a)

The defect depicted in FIG. 4(a) acts like a negative lens and will produce the signal shown in FIG. 4(b) assuming a downward scan. As can be seen, the signal first goes above the general level in the region at 31 and then below the general level in the region at 32. It should be noted that this is in contrast to the previous case where the signal went downward first and then upward. A seed or blister would produce this same general appearance of a signal. Thus, it can be seen that the characteristic signal provides a means to discriminate between the two types of defects, depending upon whether the signal goes positive or negative to the general signal level, first in the scan.

The rays 25 from the brightest part of the diffuser will be refracted by the region 31 into the camera and the rays 23 from the darkest part of the diffuser will be refracted into the camera by region 32.

Figure 5A:
FIG. 5(a) is a partial cross-sectional view on an enlarged scale through a bottle wall having an exaggerated refractive variation.
Figure 5B:
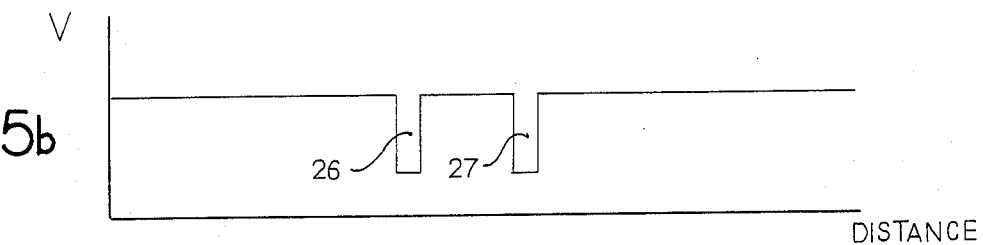
FIG. 5(b) is an illustration of the output level of a camera viewing the 5(a) wall with a sharp edge mask and uniform diffuse illumination.
Figure 5C:
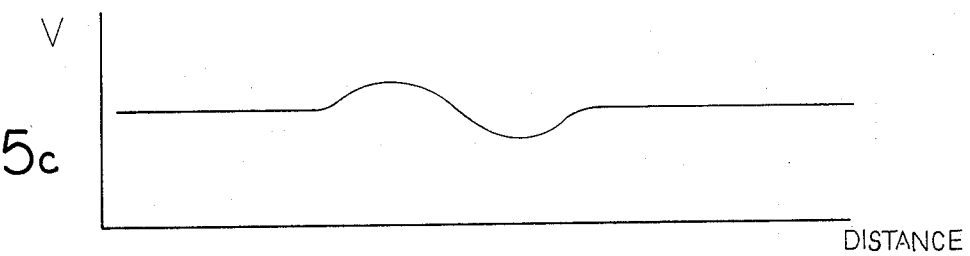
FIG. 5(c) is an illustration of the output level of a camera viewing a FIG. 5(a) variation with the gradient illumination source of the invention.

The gradient type light source of the invention gives a signal which varies smoothly rather than abruptly with normal refractive variations of the inspected object. Such a normal refractive variation is illustrated in FIG. 5(a), but greatly exaggerated for illustration purposes and to show how a "hard-edged" uniform light source would respond to such a variation. If a hard-edged uniform light source were used, the signal would be almost "binarized". If the slope of the normal refractive variation were large enough, it would deflect the line of sight of the camera off the light source and the region would look black with an abrupt transition. The signal produced by the "hard-edged" source will show two dark regions where the slope of the refractive region is the greatest. This is illustrated in FIG. 5(b) with the two square wave signals 26 and 27. The problem with this type of light source is that it must be made large enough so the hard edges of the mask can be far enough away so that normal refractive variations are not seen and still be able to pick up defects. These, unfortunately, work in opposite directions. The signal is of higher frequency content, with more abrupt transitions than the more gently varying signal produced by the illumination with a gradient source, as illustrated in FIG. 5(c).

Figure 6A:
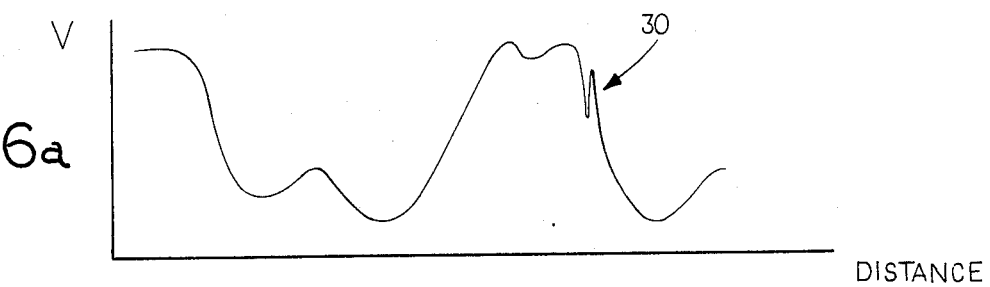
FIG. 6(a) is a typical camera signal output when viewing a defective bottle.
Figure 6B:
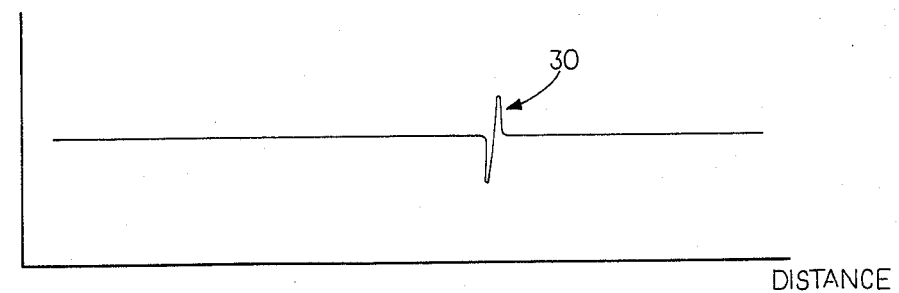
FIG. 6(b) is the signal of FIG. 6(a) after being filtered.

Defects are almost always smaller in extent than the normal refractive variations of blown ware. An illustration of a typical signal from a camera that is seeing a defect which has been illuminated by a gradient source is shown in FIG. 6(a). The defect signal is designated 30. By filtering the signal shown in FIG. 6(a), one can obtain a quiet base line, which is the result of removal of the background fluctuations due to normal refractive variations, and the more rapidly varying defect signal 30 can then be easily detected.

The diffuse light source S shown in FIGS. 1 and 2 is long in the direction parallel to the bottle movement on a conveyor 31 and has no gradient in this direction. Thus, because of the space invariance of the source, the system of the invention will work for any position of the bottle to the right or left in FIG. 1 as long as it is within the area of illumination. The described refractive functions are only significant in the vertical plane along the axis of illumination. Thus, the bottle can be inspected by simply translating through the camera view with the camera scanning along successive chords as the bottle moves. Since the outer edges of the bottle will not actually be viewed but appear as dark refracted areas and the electronics is such as to provide a signal output when the viewable sides of the bottle are in position, the bottle should be turned 90° and run through the system again for full coverage.

Each point on the diffuse source 10 will generate a family of rays emanating from the entire surface of the lens 12 and which will be traveling parallel to a line from that point through the center of the lens. Each point on the source will generate such a family with directions defined by the difference in location of the point on the source in relation to the center of the lens. This results in the generation of an angular spectrum of light which is the same for all locations in front of the lens; i.e., space invariant illumination. This spectrum of light angles is the thing being chosen by the illumination system of the invention. One chooses this spectrum for giving the greatest enhancement of the types of refractive defects one wants to detect while eliminating the gradual sloping irregularities that would normally be refracted by specular light. If the source were diffuse and uniformly bright all refractive defects would be washed out and one would not see anything. It should be pointed out also that the camera in the present description of the invention is looking at the vertical slices of the object as the object moves through the field of view.

Thus, it can be seen with the foregoing system that the angular spectrum produced by the illumination system of the invention will result in a highly sensitive illumination system for determining the presence of sharp refractive defects while suppressing the appearance of more gradual surface discontinuities that might be present in, for example, a glass container or other transparent glass article being moved through the view of the camera 17. Further, the system will provide a means to discriminate between blisters and some surface type refractive defects because of the gradient intensity of illumination.

What is claimed:

1. In a method of inspecting transparent objects for defects wherein a generally planar diffuser acts as a source of diffuse light is positioned at the focal length F of a lens thereby producing, in front of the lens, collimated beams that originate from points on the source and the angular spectrum of illumination in front of the lens is limited to angles which are equal to or less than the angle between a line extending from the upper edge of the diffuser through the center of the lens and the central axis of the lens, and objects to be inspected are positioned normal to the lens axis in front of the lens, optically enhancing defects in the object, the improvement therein comprising back lighting the diffuser so as to produce a light intensity gradient on the diffuser which is vertical in direction, thereby providing grey scale illumination for discriminating types of these defects from gradual refractive variations, and viewing the objects with a linear array camera focused on the surface of the object to detect defects by variations in the level of light received by the camera.

2. In the method of inspecting transparent articles such as glass containers for optically refractive or absorptive defects having steep acceptance angles and discriminating against more gradual refractive variations wherein the articles are backlighted as they are moved in a linear upright path in front of a viewing camera having a vertical linear array of pixels for receiving light focused from the vertical wall of the article, the improvement in the backlighting of the article comprising the steps of forming a source of diffuse illumination in back of the article, said source having a vertical gradient of brightness over its surface, placing a first convex or Fresnel lens in front of the source at a distance from the source so as to provide an angular spectrum of collimated light coming from the lens directed toward the article, imaging the light passing through the first lens and article by a second lens into a plane in the region of the aperture of a vertical, linear array camera, focusing the camera on the article to be inspected and obtaining a signal representative of successive vertical sweeps of the array in the camera as the articles move between the two lenses.

3. The method of claim 2 further including the step of filtering the background noise of low frequency from the signal to give an indication of the refractive defect in the article.

4. An apparatus for inspecting glass articles for refractive defects wherein the glass articles are illuminated from the back as they move through an inspection zone and are viewed from the front by a camera having a linear, vertical, array of light sensitive pixels, illumination of the refractive defects to enhance the defects comprising a source of diffuse light, a first convex lens in front of the source and spaced therefrom a distance so as to produce a spectrum of collimated light extending from the lens through the inspection zone to thereby provide illumination to a defective article which will be refracted from the field of view of the camera due to the refractive defect, the improvement in said illumination comprising means for producing a vertical gradient of brightness in said diffuse source, a second lens between the camera and the article for imaging the collimated light in a plane adjacent said camera, said camera having an aperture and lens focused on the article whereby light in the camera is enhanced or diminished depending upon the direction that a refractive defect in the article deflects the light from the gradient source.

5. The apparatus of claim 4 further including means connected to said camera for providing a signal output whose amplitude is responsive to relative brightness and the slope of the light refractive areas of the article.

6. The apparatus of claim 5 further including filter means connected to said signal output for removing the signals that are of a low frequency from those of high frequency that are related to defects in the article.

* * * * *